(12) United States Patent
Gorin

(10) Patent No.: US 9,386,677 B1
(45) Date of Patent: Jul. 5, 2016

(54) PLASMA CONCENTRATION APPARATUS AND METHOD

(71) Applicant: Georges J. Gorin, Novato, CA (US)

(72) Inventor: Georges J. Gorin, Novato, CA (US)

( * ) Notice: Subject to any disclaimer, the term of this patent is extended or adjusted under 35 U.S.C. 154(b) by 214 days.

(21) Appl. No.: 14/334,579

(22) Filed: Jul. 17, 2014

Related U.S. Application Data

(63) Continuation-in-part of application No. 14/083,243, filed on Nov. 18, 2013, now Pat. No. 8,841,574.

(51) Int. Cl.
*B23K 10/00* (2006.01)
*H05H 1/24* (2006.01)

(52) U.S. Cl.
CPC .................................... *H05H 1/24* (2013.01)

(58) Field of Classification Search
CPC ............. H05H 1/24; H05H 1/30; H05H 1/34; H05H 2001/4645; A61L 2/14; B01J 19/129
USPC .......................... 219/121.43, 121.44, 121.59; 118/723 ME, 723 ER, 723 MP, 723 L; 156/345.35, 345.48
See application file for complete search history.

(56) References Cited

U.S. PATENT DOCUMENTS

| | | | |
|---|---|---|---|
| 5,814,154 A | 9/1998 | Boitnott et al. | |
| 5,976,992 A * | 11/1999 | Ui | C23C 16/401 427/561 |
| 6,112,696 A * | 9/2000 | Gorin | H01J 37/32357 118/723 ER |
| 6,207,587 B1 * | 3/2001 | Li | H01L 21/28185 257/E21.193 |
| 6,267,074 B1 * | 7/2001 | Okumura | C23C 16/5096 118/723 ER |
| 6,692,649 B2 | 2/2004 | Collison et al. | |
| 6,726,803 B2 * | 4/2004 | Kondo | H01J 37/32082 118/723 E |
| 6,828,241 B2 | 12/2004 | Kholodenko et al. | |
| 7,015,415 B2 | 3/2006 | Gorin | |
| 7,315,346 B2 | 1/2008 | Van Beek et al. | |
| 7,393,432 B2 | 7/2008 | Dhindsa et al. | |
| 2012/0034137 A1 | 2/2012 | Risby | |

* cited by examiner

*Primary Examiner* — Mark Paschall
(74) *Attorney, Agent, or Firm* — Kevin Roe

(57) ABSTRACT

An apparatus and method to concentrate a plasma from one or more plasma sources through at least one pathway. A first embodiment of the invention involves a method to concentrate a plasma for treating one or more articles with a selectively concentrated plasma generated from dissociating one or more gases, the method includes supplying one or more gases from a source to a first chamber; applying RF power to dissociate the one or more gases and create a plasma; withdrawing the dissociated one or more gases from the first chamber through at least one pathway; and supplying the dissociated one or more gases to a treatment chamber containing one or more articles, wherein the at least one pathway selectively concentrates the plasma in the at least one pathway by using a narrower pathway with a volume smaller than the treatment chamber to restrict the diffusion of the plasma to concentrate the plasma. A second embodiment of the invention involves an apparatus to concentrate a plasma to treat one or more articles.

20 Claims, 12 Drawing Sheets

PLASMA CONCENTRATION APPARATUS AND METHOD

CROSS-REFERENCE TO RELATED APPLICATIONS

This application is a continuation-in-part of a U.S. utility patent application Ser. No. 14/083,243, filed Nov. 18, 2013, entitled "Plasma Extension and Concentration Apparatus and Method," by the same inventor, that issued on Sep. 23, 2014, as U.S. Pat. No. 8,841,574, which is hereby incorporated by reference.

BACKGROUND OF THE INVENTION

1. Field of the Invention

This invention relates to the use of a plasma or a glow discharge for dissociating one or more gases into reactive and non-reactive ionic and reactive and non-reactive neutral species, and in particular, to concentrating such a plasma.

2. Description of the Prior Art

Plasma apparatus can be divided into two broad categories, downstream or remote plasma and direct plasma. In downstream plasma, the article(s) are not immersed in the glow discharge, as it is in direct plasma. The result is a purely chemical and multi-directional process resulting in a somewhat more gentle treatment of the article(s) because high power electromagnetic waves at high frequency are not coupled through the article(s) and there is no heating from direct ion bombardment. In either type of apparatus, it is known in the art to employ some type of plasma for processing one or more article(s).

Typically, one or more reactive gases (such as air, oxygen-based gases, or halogen-based gases, including fluorine, chlorine, bromine, or other equivalent gases, as well as gas molecular compounds having one or more oxygen or halogen atoms), are used in combination with other gases, due to the highly reactive nature of the reactive gas(es) in a plasma chamber.

In the prior art, in downstream (remote) plasma processing, the problems encountered regarding the article can include: high energy photons reaching the surface of the article, electrical charges reaching the surface of the article, or a decrease in the concentration of reactive neutrals caused by diffusion of reactants throughout the entire volume of the vacuum chamber. For example, the prior art tries to remove the photons with passageways between the plasma exhaust of the plasma source and the article, where the passageway has an elbow (a bend of 90 degrees) or baffles (which increase the distance between the source and the article in a convoluted manner) to prevent photons from reaching the article. And the prior art also attempts to remove the electrical charges by means of recombining electrical charges in plasma, depending on the distance between the exhaust of the plasma source and the surface of the article.

However, the prior art relies on the plasma parameters (i.e., dissociating power and pressure) of the plasma source in order to extend the plasma. But once the maximum power available and minimum operating pressure are reached, the prior art falls short in concentrating a plasma for treating articles downstream. In view of the foregoing, what is needed is an improved method and apparatus to efficiently and selectively concentrate a plasma to direct it at an article.

SUMMARY OF THE INVENTION

The present invention includes a pathway coupled to the exhaust side of the discharge chamber or plasma chamber containing one or more gases, where concentration of the plasma can be achieved when the plasma extends past the exhaust of the plasma discharge chamber, to reach the article. In one embodiment of the invention, one or more gases are dissociated, which could include one or more inert gases and one or more reactive gases (e.g., air, or a oxygen-based or halogen-based gas) with or without other gases. The invention can be implemented in numerous ways, such as by a method, an apparatus, or a plasma system. Four aspects of the invention are described below.

A first aspect of the invention is directed to a method for treating one or more articles with a selectively concentrated plasma generated from dissociating one or more gases. The method includes supplying one or more gases from a source to a first chamber; applying RF power to dissociate the one or more gases and create a plasma; withdrawing the dissociated one or more gases from the first chamber through at least one pathway; and supplying the dissociated one or more gases to a treatment chamber containing one or more articles, wherein the at least one pathway selectively concentrates the plasma in the at least one pathway by using a narrower pathway with a volume smaller than the treatment chamber to restrict the diffusion of the plasma to concentrate the plasma.

A second aspect of the invention is directed to a method for treating one or more articles with a selectively concentrated plasma generated by dissociating one or more gases. The method includes supplying one or more gases from a first source to a first chamber, applying RF power to dissociate one or more gases in the first source and create a first plasma, withdrawing the first plasma from the first chamber through a first pathway and selectively concentrating the first plasma with a first pathway; supplying one or more gases from a second source to a second chamber for RF power to dissociate the one or more gases from the second source to create a second plasma; using a second pathway to withdraw the second plasma from the second chamber and selectively concentrating the second plasma with the second pathway; and supplying the concentrated first plasma from the first chamber and concentrated second plasma from the second chamber to a treatment chamber containing one or more articles, wherein at least one pathway selectively concentrates the plasma in the at least one pathway by using a narrower pathway with a volume smaller than the treatment chamber to restrict the diffusion of the plasma to concentrate the plasma.

A third aspect of the invention is directed to an apparatus to dissociate one or more gases to produce a plasma. The apparatus includes a first chamber coupled to a source of one or more gases; one or more RF energy sources coupled to the first chamber; means for disassociating the one or more gases in the first chamber into a plasma; at least one pathway; a treatment chamber coupled to the first chamber through the at least one pathway to receive the plasma, wherein the treatment chamber contains one or more articles, wherein the at least one pathway selectively concentrates the plasma in the at least one pathway by using a narrower pathway with a volume smaller than the treatment chamber to restrict the diffusion of the plasma to concentrate the plasma.

A fourth aspect of the invention is directed to an apparatus to dissociate one or more gases to produce a plasma. The apparatus includes a first chamber with a first pathway, coupled to a first source of one or more gases; a second chamber with a second pathway, coupled to a second source of one or more gases; one or more RF energy sources coupled to the first chamber and the second chamber; means for dissociating the one or more gases into a first plasma in the first chamber and for dissociating one or more gases into a second plasma in the second chamber; at least one pathway to concentrate at least one plasma from either the first chamber or from the second chamber; and a treatment chamber coupled to the first chamber and the second chamber, wherein the treatment chamber contains one or more articles, wherein the at least one pathway selectively concentrates the plasma in the at least one pathway by using a narrower pathway with a volume smaller than the treatment chamber to restrict the diffusion of the plasma to concentrate the plasma.

These and other objects and advantages of the invention will become apparent to those skilled in the art from the following detailed description of the invention and the accompanying drawings.

DETAILED DESCRIPTION OF THE PREFERRED EMBODIMENTS

Figure 1:
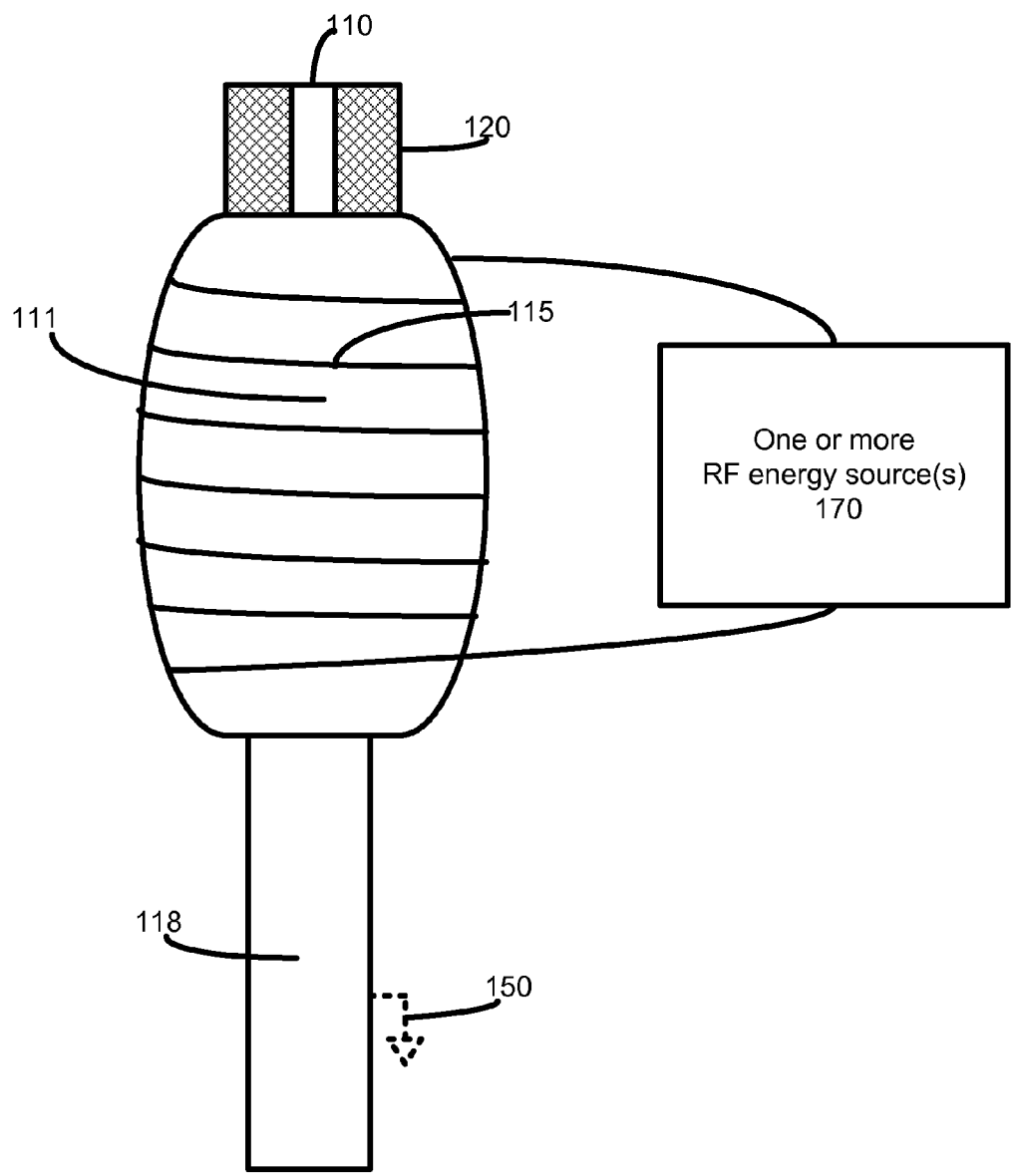
FIG. 1 illustrates an apparatus to generate and concentrate a plasma constructed in accordance with one embodiment of the invention.

The invention provides a method, an apparatus, and a system to concentrate and extend a plasma. Various embodiments of the invention can be applied to biological applications, medical applications, chemical applications, electronic applications, and any other applications where plasma can be beneficially used.

Inductive coupling or capacitive coupling can be used to couple radio-frequency (RF) electromagnetic energy to one or more gases for dissociation and creation of plasma. In this specification, drawings, and claims, radio-frequency (RF) is defined as any frequency of electromagnetic energy where inductive or capacitive coupling to a plasma can be implemented. In one embodiment, a plasma source is defined as a device that can partially ionize a gas or a mixture of gas at a reduced pressure. In one embodiment of the invention, the plasma produced can be a low temperature plasma, wherein the bulk gas temperature remain low (e.g., a few hundred degrees Celsius, more or less), while the electron temperature can be much higher (e.g., having a kinetic energy of a few hundred electron volts (eV), more or less).

What are Reactive Neutrals?

In one embodiment, the "radicals" (also called active neutrals, actives species, neutral species) have no electrical charge associated with them. The oxygen O radical, for example, can diffuse over a long distance (a few meters at 1 milliTorr) and still be chemically reactive.

Plasma Initiation Process:

The RF energy is transferred to the electrons. The electrons then partially dissociate and ionize the gas. In one embodiment of the invention operating at low power, dissociation generation of radicals occurs. A typical embodiment of the invention will convert un-reactive gas molecules into very reactive radicals. Most plasma surface chemistry is accomplished by radicals, such as the following examples (where "e−" represents an electron).

$$e\text{−} + O_2 \Rightarrow O + O + e\text{−} \tag{1}$$

$$e\text{−} + CF_4 \Rightarrow CF_3 + F + e\text{−} \tag{2}$$

Ionization

Ionization of gas molecules will typically result in the production of ions and electrons, such as the following examples.

$$e\text{−} + O_2 \Rightarrow O_2^+ + 2e\text{−} \tag{3}$$

$$e\text{−} + Cl_2 \Rightarrow Cl_2^+ + 2e\text{−} \tag{4}$$

$$e\text{−} + Ar \Rightarrow Ar^+ + 2e\text{−} \tag{5}$$

Dissociative Ionization

Dissociative ionization can also occur as well in one collision.

$$e\text{−} + CF_4 \Rightarrow CF_3^+ + F + 2e\text{−} \tag{6}$$

$$e\text{−} + O_2 \Rightarrow O^+ + O + 2e\text{−} \tag{7}$$

As mentioned before, one goal of this invention is to increase the amount of reactants that reach the surface of an article located downstream from the plasma source into a vacuum chamber. One embodiment of the invention directs the reactants towards the surface of the article before they can diffuse into the whole chamber and become diluted (thus resulting in a lower reactant density).

Passive Plasma Concentrator

When a plasma is used to remove hydrocarbons or modify the surface of polymer article from being hydrophobic to hydrophilic in an existing system, there is not a choice about the positioning of the plasma source on the vacuum chamber. The plasma source has to be connected to whichever vacuum ports are available on the vacuum chamber system.

If and when the entire internal surface of the vacuum chamber has to be cleaned, then there is little need for a concentrator. But if a specific area within the vacuum chamber needs to be cleaned, then it can be advantageous to use a concentrator so that the diffusion of the reactants into the volume of the chamber starts at the end of the concentrator and not at the end of the plasma source. It is also important to note that the benefit of the concentrator can be measured by comparing the time it takes to clean a certain area with and without the concentrator, whether there is direct line of sight or not between the end of the source and the area to be cleaned.

The passive concentrator has at least one purpose—to insure that the diffusion into the entire chamber starts near the area or the sample to be cleaned. None of the prior art mention this purpose. The prior art instead discuss plasma generation, uniformity, density and chemistry techniques. The following examples will help clarify the inventive concept.

Example 1

No Plasma Confinement and No Concentration

If there is no concentration and it is assumed that a source delivers A reactant per cubic centimeter (cm), and the chamber with an article is assumed to be a spherical chamber with a radius of 10 cm. Then the volume of that chamber would be $V1=4/3*3.1416*10^3=4,189$ cubic cm. If the plasma is operating in the molecular flow (1 mT to 10 mT pressure) and in that regime the gas diffuses equally in every direction, the density on the chamber wall will be: $D1=A/4,189$ or a reduction of approximately 4000.

Example 2

With Plasma Confinement and Concentration

If there is concentration and it is assumed that a source delivers A reactant per cubic cm, and it is assumed that there is a tube 18 centimeters long with a radius of 2 cm sticking into the same spherical chamber with a radius of 10 cm, then the volume of the confinement tube=$V2=(3.1416*2^2)*18=226$ cubic cm and the volume of a 2 cm radius sphere=$V3=(4/3)*3.1416*(2^3)=33.5$ cubic cm. As a result of the above assumptions, the density of radicals above the article on the reactor wall now is: $D2=A/(226+33.5)=A/260$. This is much less of a dilution than the factor of more than 4000 for the first example with no concentration. In order for the plasma density number to be equal at the surface of the article, the losses in the confinement tube (due mainly to collisions on the inner wall of the tube) will have to be such that only $1/15$th of the reactive chemical survive to reach the surface of the article. In most cases, such losses would not be likely, e.g., with a quartz tube and an oxygen-based plasma.

In one embodiment, another important consideration is the ability to operate over a large pressure range (hundreds of milliTorr to less than 1 milliTorr). The low pressure range (less than 1 milliTorr) provides a long mean free path (e.g., 5 centimeters at 1 milliTorr) needed if the distance from the plasma source to the article is greater than a few centimeters. In various embodiments, the lower the pressure, the farther the diffusion of reactants and the easiest the implementation of electrostatic and electromagnetic coupling to the plasma downstream from the source, since the plasma will automatically have a tendency to expand downstream.

Typical design considerations for the pathway in one embodiment would include:

1. The cross-sectional area is sized according to the size of the article, keeping in mind that as the cross-sectional area becomes larger, the concentration/density of reactant becomes lower.
2. The length of the pathway should be such that the amount of reactants diffusing away from the article (into the article's treatment chamber) is kept to a desirable amount.
3. The combination of cross-sectional area of the pathway and the length of the pathway determine the conductance of the pathway and this also affects the diffusion of reactant to the surface of the article in the treatment chamber. The diffusion also depends on the pressure regime at which the treatment chamber of the article operates (e.g., viscous flow, molecular flow or transition flow, and equivalent parameters).

Alternative embodiments are possible, but in one embodiment there are three specific goals for the materials in a pathway:

1. The material should be a non-conductor of the RF current for the frequency at which the plasma source operates.
2. The material exposed to the radicals must be inert to them and have a low recombination rate for the radicals.
3. The surface finish of the material should also be smooth to minimize the surface area of material at the molecular level.

For oxygen and a plasma radio-frequency set at 13.56 MHz, in one embodiment at least one or more of the following can be used in a pathway:

1. Hard anodized aluminum with a water seal
2. Quartz
3. Nickel plated aluminum
4. Stainless steel
5. SiO2 coated metals which would otherwise be prone to oxidizing and thus depleting the oxygen O radicals.

For fluorine and a plasma radio-frequency set at 13.56 MHz, in one embodiment at least one or more of the following can be used in a pathway:

1. Hard anodized aluminum with a water seal
2. Teflon coated hard anodized aluminum with a water seal
3. Ceramics
4. Teflon coated ceramic
5. Nickel plated aluminum
6. Stainless steel
7. Quartz can only be used if the temperature is kept below approximately 40 Celsius, otherwise it will react and deplete the fluorine.

The working pressure is function of the distance between the plasma source and the article so what is important is the minimum pressure at which the system can work. In one embodiment of the invention, a typical useful plasma would have the following characteristics.

1. One typical useful plasma provides a high reactant density at low pressures (e.g., a pressure in the range of few milliTorr (e.g., less than 10 milliTorr) when the distance between the source and the article in the treatment chamber is large (e.g., 1 meter or more), in addition this type of plasma has a pressure range that is compatible with high vacuum systems and the mean free path and diffusion rate of the gas are very large in this pressure range. For example, 50 millimeters is the mean fee path for air at 1 milliTorr, as opposed to a mean free path of 0.5 millimeter at 0.1 Torr.
2. In one embodiment the source of plasma allows concentration in pathways that are not frequency dependent, but sized to optimize the concentration of reactants at the surface of the article in the treatment chamber (e.g., the diffusion and density of reactants that are delivered by the source)

For a practical implementation, it should be noted that both electrostatic and electromagnetic couplings rely upon the presence of electrons to function. Therefore the lower the pressure, the easier it is to expand the plasma with electrons and ions present. For example, if in one embodiment, one operates in the pressure range of 1 milliTorr, then in this embodiment the length of the pathway can be in the order of one meter and its diameter can be 2.5 centimeter (cm) to 5 cm to provide a good diffusion of the radicals. For embodiments of the invention with shorter lengths (e.g., 20 cm), a smaller diameter can be used (e.g., 2.5 cm), but here the dimensions must be chosen so that the conductance of the pathway at the operating pressure is high enough to allow good diffusion of the radicals. In one embodiment, at least one 90 degree bend (or a chicane) in the pathway can be included if there is a need to prevent the photons from reaching the surface of the article, since without this bend the pathway would provide a "direct line of sight" for the photons. The purpose of the 90 degree bend is not only to remove the photons, but also so there is no direct line of sight between the exhaust of the plasma source and the article or area to be cleaned in the treatment chamber.

For the purpose of this invention, the article to be treated with plasma is considered to be far from the plasma source, where a large amount of reactive species can diffuse away from the surface of the article in the treatment chamber. Therefore, one need is to be able to transport and confine a large amount of active species from a plasma source to an article in the treatment chamber when the distance between the source and the article is large and/or if there is no direct line of sight. One device takes the form of a tube (e.g., a tube such as a quartz tube for oxygen plasma or an equivalent) so that the active species will be confined by the inside volume of the tube, which can be chosen to be much smaller than the volume of the treatment chamber containing the article. In other words, the pathway is designed to have a much smaller volume than the vacuum chamber so that the concentration of reactants at the article surface or area to be cleaned in the vacuum chamber is increased, as compared to not having such a pathway, by forcing the diffusion in the chamber to start at the exit end of the pathway located near the article's surface, instead of at the exit end of the plasma source which is located farther away from the surface of the article. This ultimately results in an increased density (concentration) of reactants at the surface of the article.

Various embodiments of the present invention physically confine the active species to the inner volume of the pathway, and also provide various means to concentrate the plasma.

It should be noted that both the distance from one end of the pathway to the exhaust of the plasma source and the distance of the opposite end of the pathway to the surface of the article in the treatment chamber provide a means for controlling the amount of charge species reaching the surface of the article in the treatment chamber. It should also be noted that in some embodiments of the invention, the pathway provides a RF ground return path. Therefore, in some embodiments of the invention, a conductive metal is included in the construction of the pathway, but in alternative embodiments the pathway can be coated with various materials (or an insert can be used) in order to minimize the loss of reactive neutrals on the inner surface of the pathway.

Figure 3:
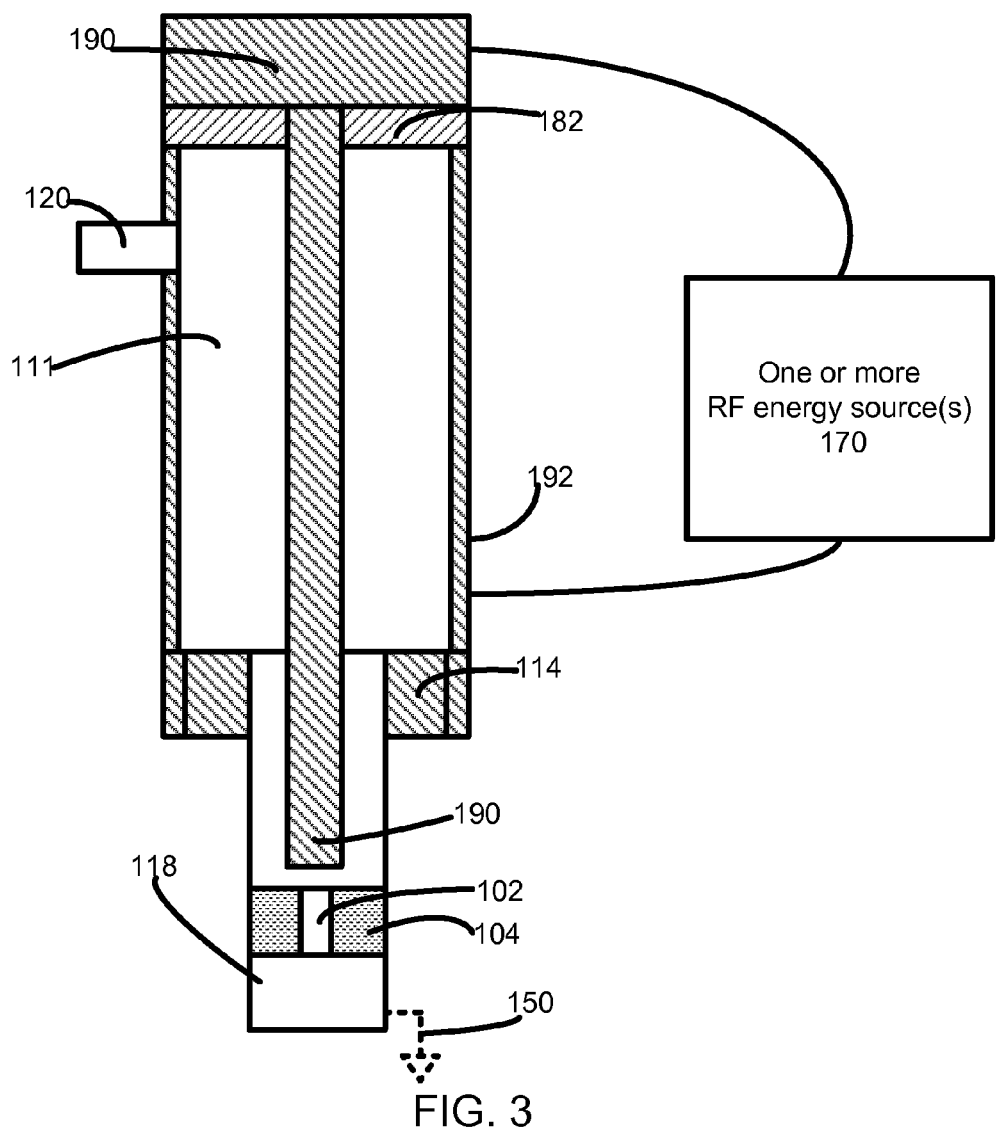
FIG. 3 illustrates an apparatus to generate and concentrate a plasma constructed in accordance with an alternative embodiment of the invention.

In FIG. 1, a plasma generating discharge chamber includes a gas inlet 120 which supplies one or more gases to discharge chamber 111. Discharge chamber 111 also has a capillary tube 110 to prevent plasma expansion into gas inlet 120. One or more radio-frequency (RF) energy sources 170 are coupled to inductor 115, which surrounds discharge chamber 111 and dissociates one or more gases passing through discharge chamber 111, which may be made of various materials (e.g., a dielectric material or an equivalent). Discharge chamber 111 is coupled to an article in a treatment chamber (not shown) by a pathway 118. The pathway 118 in various embodiments can also have an optional ground 150 (shown in dotted lines) near the exhaust of the plasma source to terminate the RF leaking from the source as the plasma expands. Pathway 118 is optionally grounded to concentrate the plasma down the pathway further than the plasma source alone would allow, since the RF field will diverge and terminate on the surfaces of the chamber containing the article(s). In one embodiment of the invention, the plasma source would include a constriction (as shown in FIG. 3), such as described in an earlier patent application by the same inventor, entitled "Higher Power Density Downstream Plasma," Ser. No. 10/781,226, filed on Feb. 18, 2004, and issued as U.S. Pat. No. 7,015,415 on Mar. 21, 2006, which is hereby incorporated by reference.

In various embodiments, the pathway 118 can be fabricated from non-conducting materials (e.g., quartz, glass, ceramics, or a combination, or an equivalent material). In one embodiment, the pathway 118 includes coils including electrically conductive metal with a diameter ranging from one eighth of an inch (~0.3 centimeters) to one quarter of an inch (~0.6 centimeters).

Figure 2:
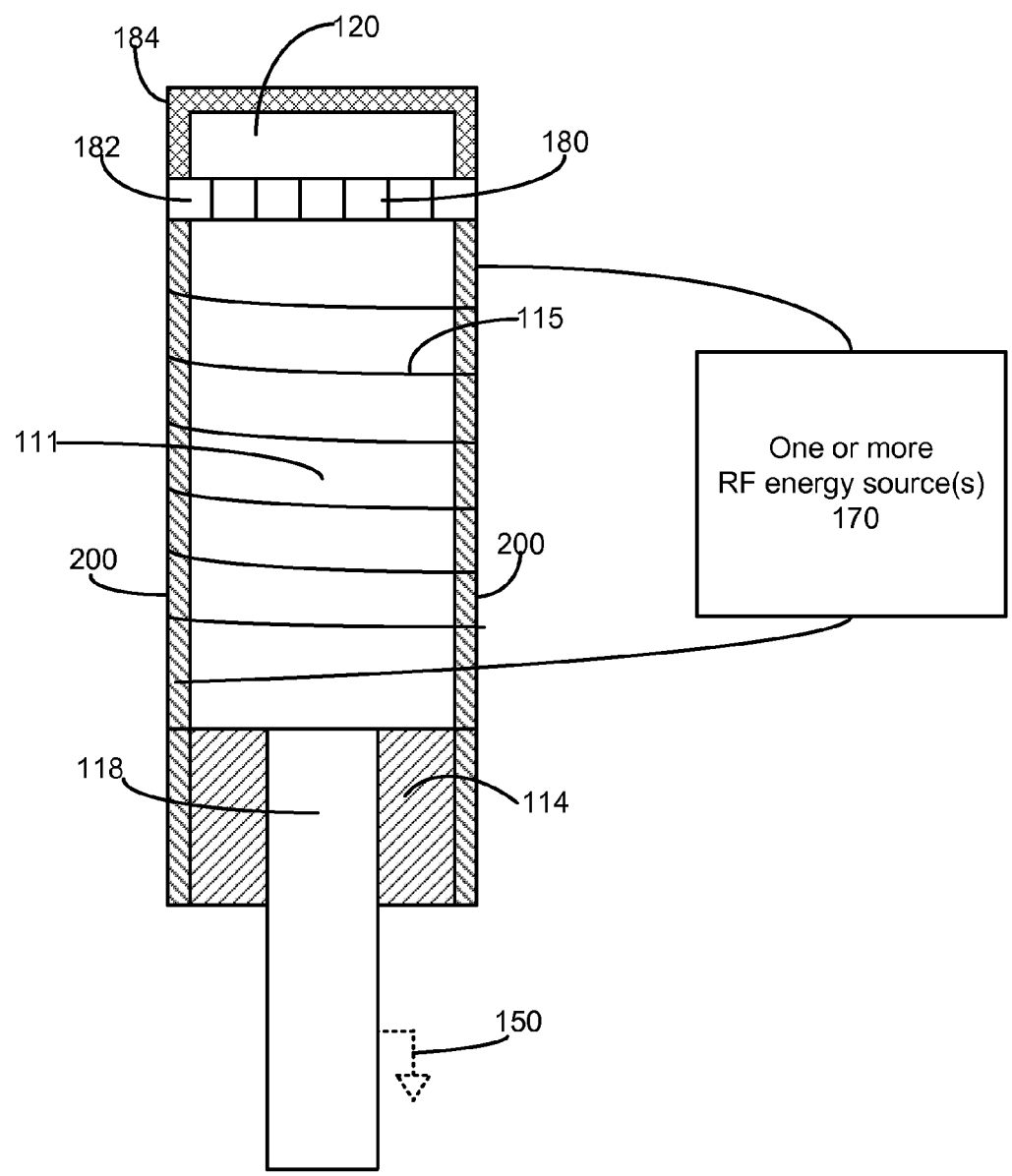
FIG. 2 illustrates an apparatus to generate and concentrate a plasma constructed in accordance with an alternative embodiment the invention.

In FIG. 2, a plasma generating chamber has a gas inlet 120 which supplies one or more gases to discharge chamber 111. A metal or dielectric material 184 encloses gas inlet 120 and a dielectric layer 182 has small openings (e.g., holes, slots, or equivalent perforations) 180 to prevent plasma expansion upstream from discharge chamber 111 through gas inlet 120. One or more RF energy sources 170 are coupled to inductor 115, which surrounds discharge chamber 111 and dissociates one or more gases passing through discharge chamber 111. The discharge chamber walls 200 may be made of various materials (e.g., a dielectric material such as, ceramic, glass, Teflon, or an equivalent). Discharge chamber 111 is coupled to an article in a treatment chamber (not shown) by a pathway 118. The pathway 118 in various embodiments can also have an optional ground 150 (shown in dotted lines) near the exhaust of the plasma source to terminate the RF leaking from the source as the plasma expands. In various embodiments, the pathway 118 can be fabricated from non-conducting materials (e.g., quartz, glass, ceramics, Teflon, or a combination, or an equivalent material). In another embodiment, the pathway 118 includes a metal or conductive coating combined with an inside or outside layer of dielectric.

In FIG. 3, gas inlet 120 with a means to control backwards plasma expansion supplies one or more gases to discharge chamber 111. Discharge chamber 111 also has a dielectric layer 182 between the discharge chamber 111 and a first electrode 190. Both the first electrode 190 and a second electrode 192 are connected to one or more RF energy sources 170. One or more RF energy sources 170 provide the power to dissociate one or more gases passing through discharge chamber 111. The first electrode 190 can have shorter or longer lengths in different embodiments, but in this embodiment the first electrode 190 is extended so far as to partially reach inside a pathway 118. Discharge chamber 111 is coupled to an article in a treatment chamber (not shown) by a pathway 118. The pathway 118 in various embodiments can also have an optional ground 150 (shown in dotted lines) near the exhaust of the plasma source to terminate the RF leaking from the source as the plasma expands. In various embodiments, the pathway 118 can be fabricated from non-conducting materials (e.g., quartz, glass, ceramics, Teflon, or a combination, or an equivalent material) to selectively concentrate the plasma inside the pathway 118. In one embodiment of the invention, the plasma source would include a constriction 102 in an insert 104, such as described in an earlier patent application by the same inventor, entitled "Higher Power Density Downstream Plasma," Ser. No. 10/781,226, filed on Feb. 18, 2004, and issued as U.S. Pat. No. 7,015,415 on Mar. 21, 2006, which is hereby incorporated by reference.

Figures 4A, 4B:
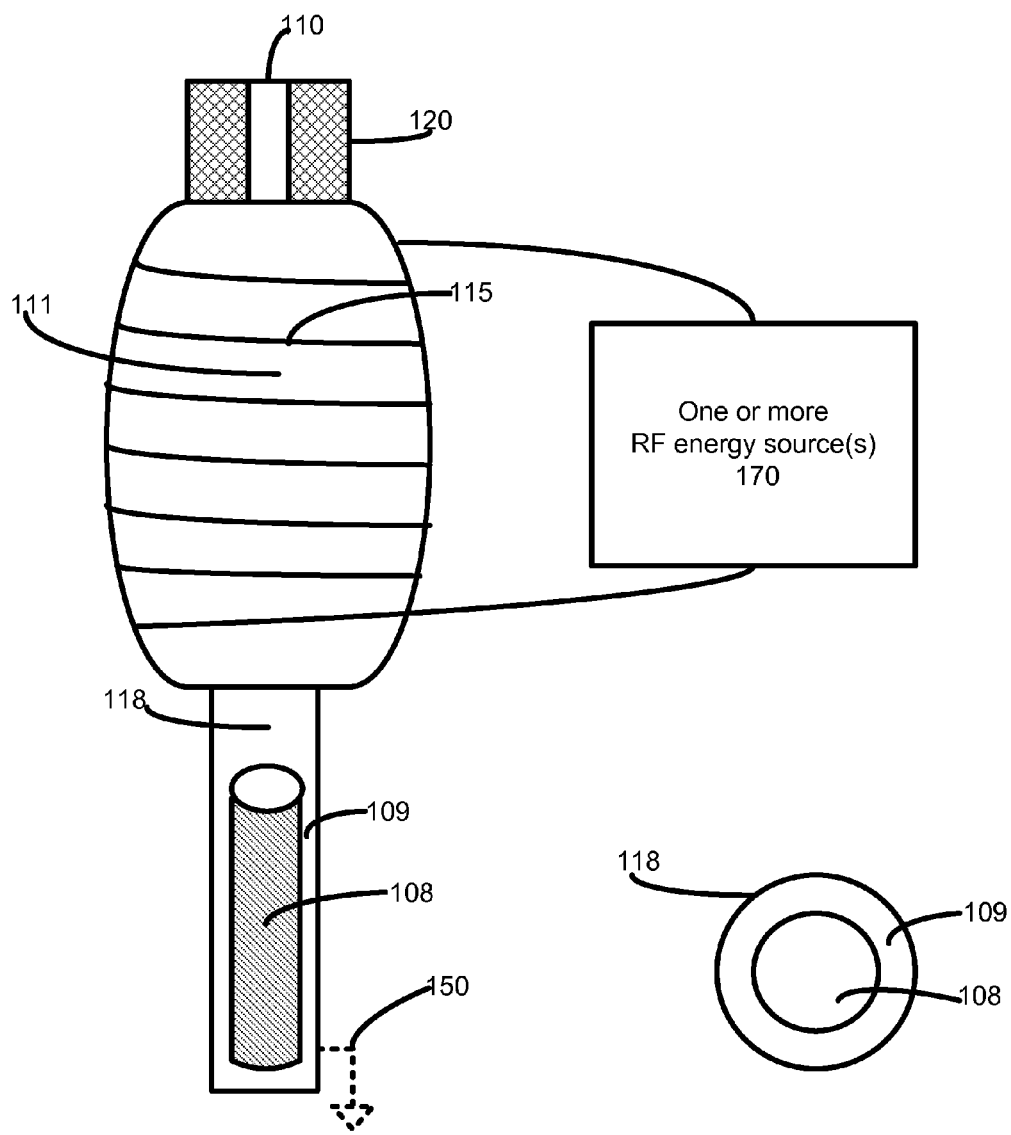
FIG. 4A illustrates an apparatus to generate and concentrate a plasma constructed in accordance with an alternative embodiment of the invention.
FIG. 4B shows a cross-sectional view of a pathway shown in FIG. 4A.

FIG. 4A illustrates an apparatus to generate and concentrate a plasma constructed in accordance with an alternative embodiment of the invention. In FIG. 4A, a plasma generating discharge chamber includes a gas inlet 120 which supplies one or more gases to discharge chamber 111. Discharge chamber 111 also has a capillary tube 110 to prevent plasma expansion into gas inlet 120. One or more radio-frequency (RF) energy sources 170 are coupled to inductor 115, which surrounds discharge chamber 111 and dissociates one or more gases passing through discharge chamber 111, which may be made of various materials (e.g., a dielectric material or an equivalent). Discharge chamber 111 is coupled to an article in a treatment chamber (not shown) by a pathway 118 (conducting in this embodiment) with a hollow inner pathway 108 and a radially thick material 109 (dielectric in this embodiment). The pathway 118 in various embodiments can also have an optional ground 150 (shown in dotted lines) near the exhaust of the plasma source to terminate the RF leaking from the source as the plasma expands.

FIG. 4B shows a cross-sectional view of a pathway shown in FIG. 4A, in accordance with one embodiment of the invention. Pathway 118 has a hollow inner pathway 108 and a radially thick material 109. One embodiment of the invention can include a pathway that is 5 centimeters to 25 centimeters long with a diameter ranging from 2.5 cm to 5.0 cm, including a hard anodized aluminum or stainless steel tube. In various embodiments, the non-conducting dielectric radially thick material 109 can be fabricated from non-conducting materials (e.g., quartz, glass, ceramics, or a combination, or an equivalent material). In one embodiment, a conducting pathway 118 can be coated on the inside surface with a material to provide a low recombination rate for radicals on the inside surface.

Figure 5:
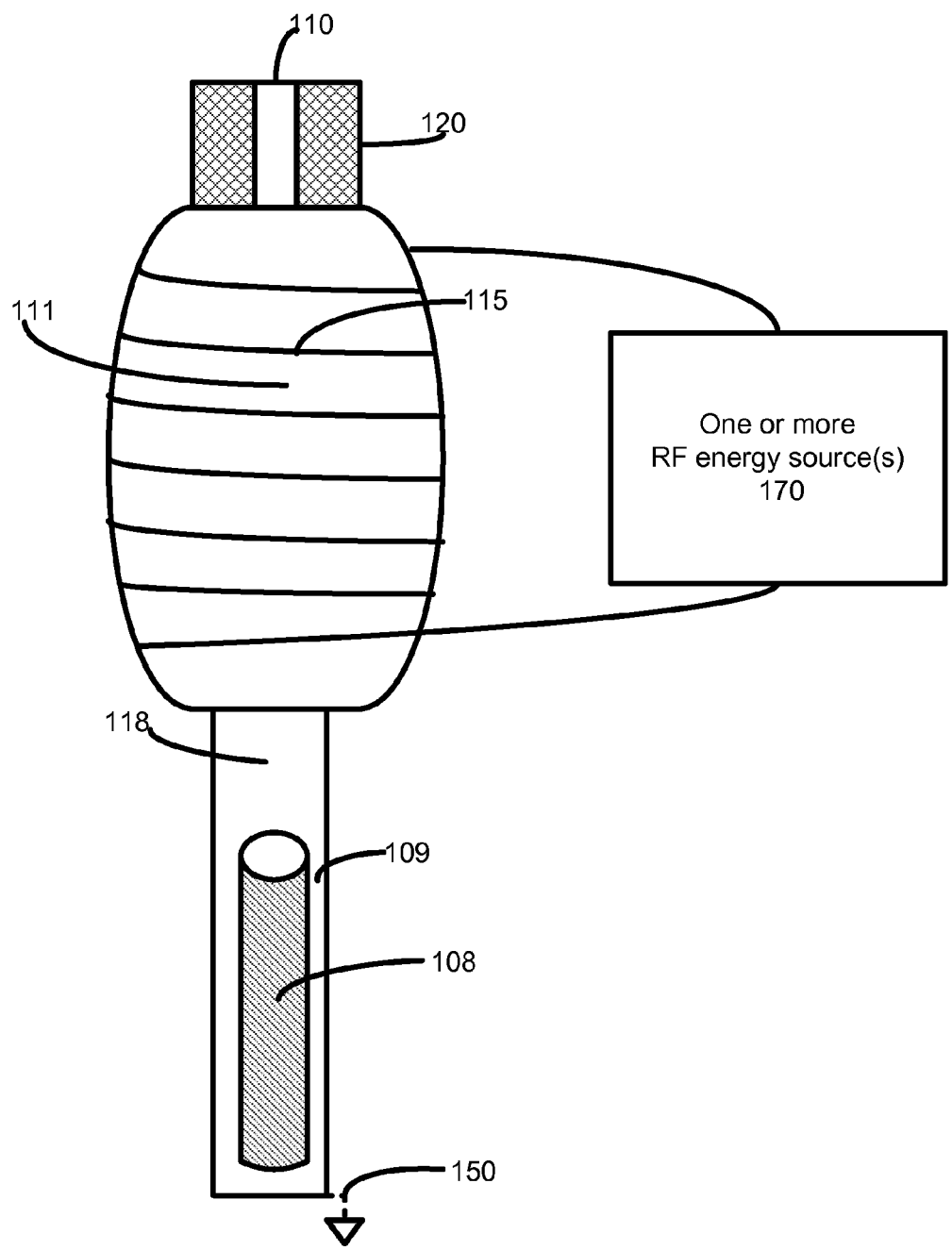
FIG. 5 illustrates an apparatus to generate and concentrate a plasma constructed in accordance with an alternative embodiment of the invention.

In FIG. 5, a plasma generating discharge chamber includes a gas inlet 120 which supplies one or more gases to discharge chamber 111. Discharge chamber 111 also has a capillary tube 110 to prevent plasma expansion into gas inlet 120. One or more radio-frequency (RF) energy sources 170 are coupled to inductor 115, which surrounds discharge chamber 111 and dissociates one or more gases passing through discharge chamber 111, which may be made of various materials (e.g., a dielectric material or an equivalent). Discharge chamber 111 is coupled to an article in a treatment chamber (not shown) by a pathway 118. This embodiment has a pathway 118 (a non-conducting dielectric in this embodiment) coupling to further increase the diffusion of the plasma toward the end of the pathway 118. The pathway 118 (dielectric in this embodiment) includes a hollow inner pathway 108 (with a metal surface coating in this embodiment) and a radially thick material 109 in the pathway 118. The pathway 118 in various embodiments can also have an optional ground 150 (shown in dotted lines) near the exhaust of the plasma source to terminate the RF leaking from the source as the plasma expands.

In one embodiment, the length of the pathway 118 ranges from 25 cm to 100 cm, and has a diameter ranging from 2.5 cm to 5.0 cm. In one embodiment, the pathway 118 includes stainless steel or hard anodized aluminum with a water seal and a coating of Teflon® or a silicon dioxide to prevent electrical contact between inner hollow pathway 108 and the pathway 118. In various embodiments, the pathway 118 can be fabricated from non-conducting materials (e.g., quartz, glass, ceramics, Teflon, or a combination, or an equivalent material) to provide a means to concentrate the plasma inside the pathway 118.

In various embodiments, the hollow inner pathway 108 can be fabricated from one or more conducting metals (e.g., aluminum, stainless steel, copper, nickel-plated copper, or a combination, or an equivalent metal) and coated on the inner lumen surface of the pathway 118 that includes an insulating material (e.g., ceramic, silicon dioxide, Teflon, or an equivalent). In alternative embodiments, the pathway 118 can be fabricated from an insulating material (e.g., ceramic, silicon dioxide, Teflon, or an equivalent) and then selectively coated with a conducting metal as previously described.

Figure 6:
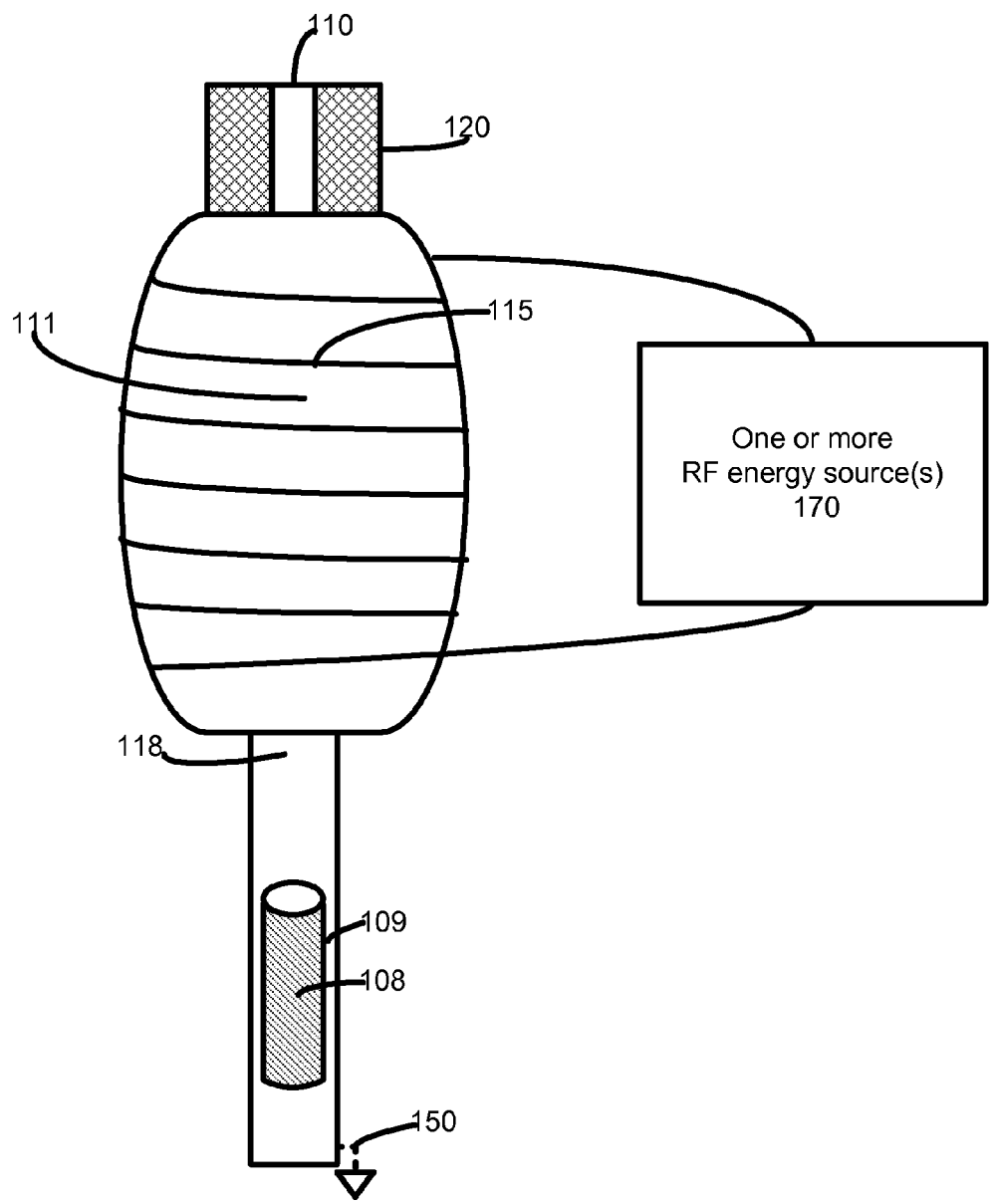
FIG. 6 illustrates an apparatus to generate and concentrate a plasma constructed in accordance with one embodiment of the invention.

In FIG. 6, a plasma generating discharge chamber includes a gas inlet 120 which supplies one or more gases to discharge chamber 111. Discharge chamber 111 also has a capillary tube 110 to prevent plasma expansion into gas inlet 120. One or more radio-frequency (RF) energy sources 170 are coupled to inductor 115, which surrounds discharge chamber 111 and dissociates one or more gases passing through discharge chamber 111, which may be made of various materials (e.g., a dielectric material or an equivalent). Discharge chamber 111 is coupled to an article in a treatment chamber (not shown) by a pathway 118 (conducting in this embodiment). The pathway 118 in various embodiments can also have an optional ground 150 (shown in dotted lines) near the exhaust of the plasma source to terminate the RF leaking from the source as the plasma expands. In one embodiment, the length of the pathway 118 ranges from 25 cm to 100 cm, and has a diameter ranging from 2.5 cm to 5.0 cm. This embodiment provide an electromagnetic coupling to further increase the diffusion of the plasma toward the end of the pathway.

In one embodiment, the pathway 118 includes stainless steel or hard anodized aluminum with a water seal and a coating of Teflon® or silicon dioxide on the inside to prevent electrical contact to the pathway 118. In various embodiments, the pathway 118 itself includes a layer of an electrically conductive metal (e.g., nickel plated copper, copper, silver, aluminum, gold, or various metal alloys or electrically conductive coatings, or equivalents).

In various embodiments, the pathway 118 can be fabricated from one or more conducting metals (e.g., aluminum, stainless steel, copper, nickel-plated copper, or a combination, or an equivalent conductor). In alternative embodiments, the pathway 118 can be fabricated from an insulating material (e.g., ceramic, silicon dioxide, Teflon, or an equivalent) and then selectively coated with a conducting metal as previously described.

Figure 7:
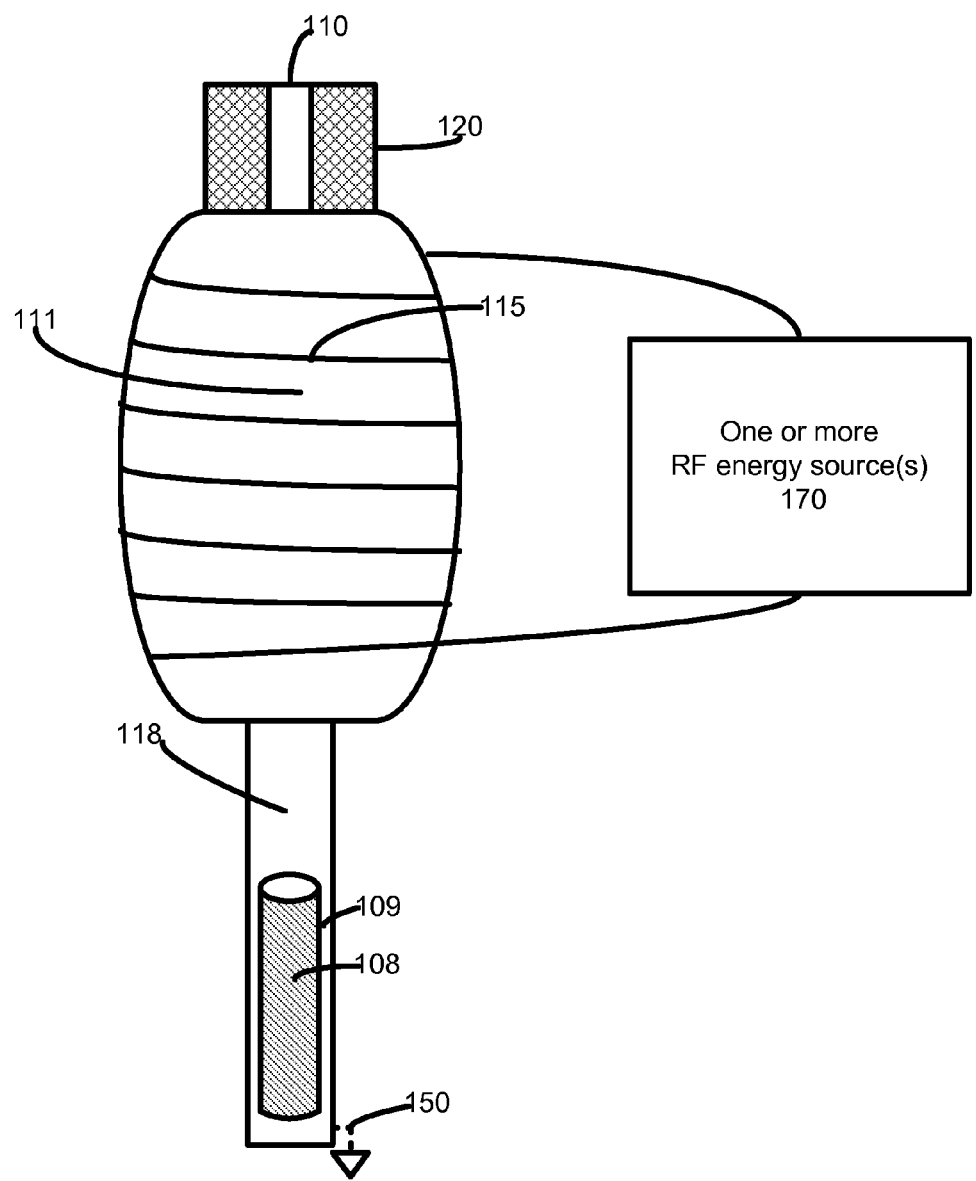
FIG. 7 illustrates an apparatus to generate and concentrate a plasma constructed in accordance with one embodiment of the invention.

FIG. 7 illustrates an apparatus to generate and concentrate a plasma constructed in accordance with one embodiment of the invention. The one or more radio-frequency (RF) energy sources, inductor, discharge chamber are not shown. The pathway 118 (non-conducting in this embodiment) has a hollow inner pathway 108 and a radially thick material 109. The pathway 118 in various embodiments can also have an optional ground 150 (shown in dotted lines) near the exhaust of the plasma source to terminate the RF leaking from the source as the plasma expands. The hollow inner pathway 108 is RF insulated from the pathway 118. In one embodiment an insulating material (e.g., silicon dioxide) is deposited inside pathway 118. In another embodiment the pathway 118 comprises a dielectric material (e.g., quartz, ceramic, Teflon, or a combination or an equivalent).

In various embodiments, the pathway 118 can have an optional ground 150 fabricated from one or more conducting metals (e.g., aluminum, stainless steel, copper, nickel-plated copper, or a combination, or an equivalent metal). In alternative embodiments, the pathway 118 can be fabricated from an insulating material (e.g., ceramic, silicon dioxide, Teflon, or an equivalent) and then selectively coated with a conducting metal as previously described.

Figure 8:
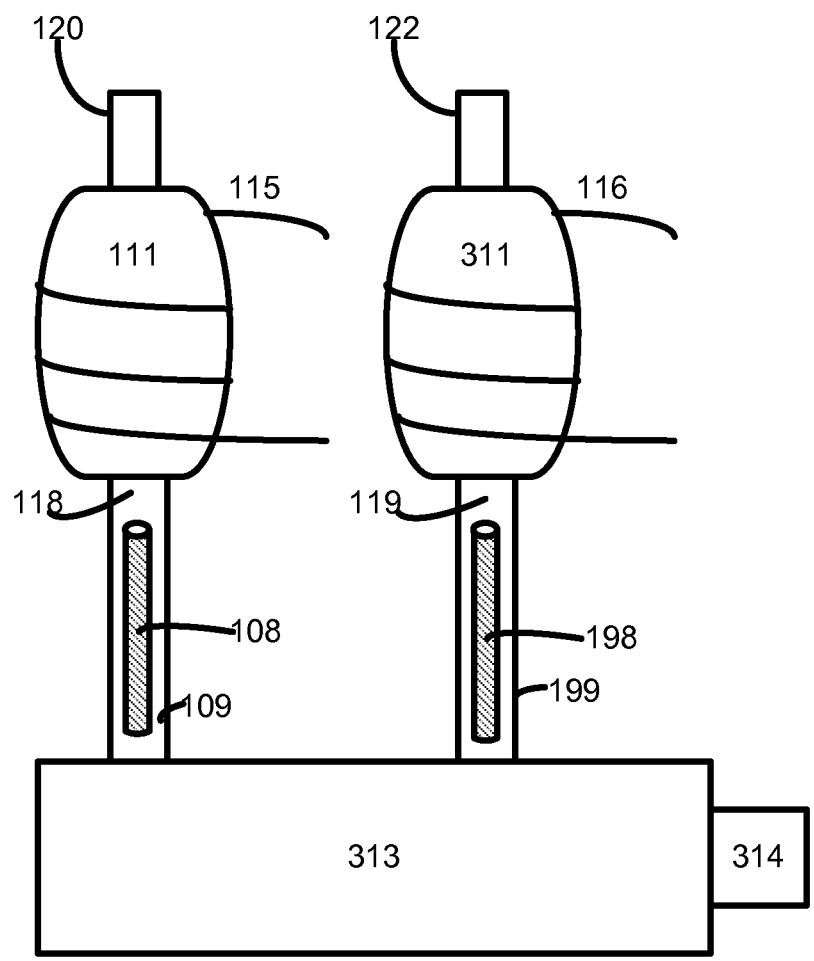
FIG. 8 illustrates an apparatus to generate and concentrate a plasma, in accordance with an alternative embodiment of the present invention, where two identical discharge chambers are coupled to a chamber for combining the plasmas from the discharge chambers.

When incompatible chamber materials and gas types occur (such as quartz and fluorine gas), multiple plasma sources can be used to dissociate each gas independently and the exhaust gas is combined to provide the desired mix of chemicals, such as in the next figure. FIG. 8 illustrates an embodiment of the invention in which the discharge chambers are essentially operating in parallel when inductors 115 and 116 are connected together to the same RF energy source(s). In an alternative embodiment, inductors 115 and 116 are connected to different RF energy source(s) to operate independently. In FIG. 8, gas inlets 120 and 122 provide one or more gases to discharge chambers 111 and 311 which are coupled to chamber 313 for combining the plasma from the discharge chambers 111 and 311 and supplying plasma to chamber 313. Inductor 115 surrounds discharge chamber 111 and dissociates the gas passing through chamber 111. Similarly, inductor 116 surrounds discharge chamber 311 and dissociates the gas passing through chamber 311. The RF power is supplied to inductors 115 and 116 by one or more RF energy sources (not shown). Discharge chamber 111 is coupled to chamber 313 by a pathway 118 and discharge chamber 311 is coupled to chamber 313 by a pathway 119. Pathway 118 has a hollow inner pathway 108 and a radial thickness of material 109. Pathway 119 has a hollow inner pathway 198 and a radial thickness of material 199.

Figure 9A:
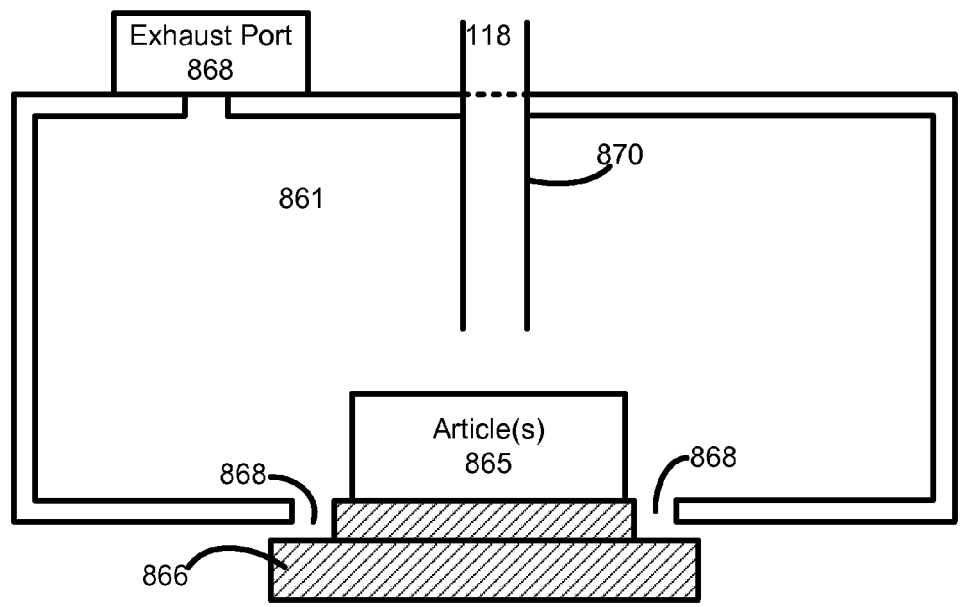
FIG. 9A illustrates a schematic cross-section of a treatment chamber for processing one or more articles, in accordance with one embodiment of the invention.
Figure 9B:
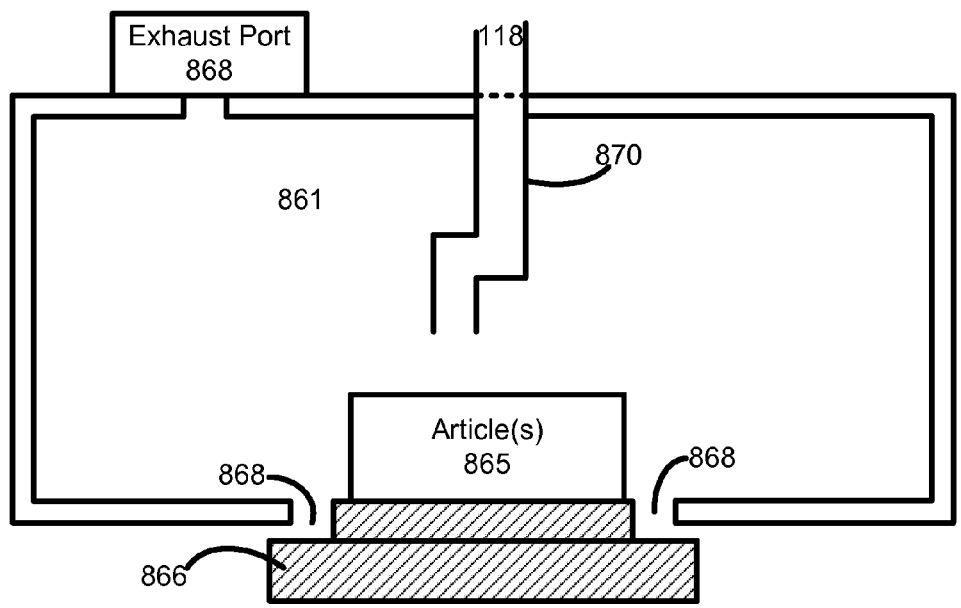
FIG. 9B illustrates a schematic cross-section of a treatment chamber for processing one or more articles, in accordance with another embodiment of the invention.

The reactive neutral species flow through pathways 118 and 119 into chamber 313, where they mix and pass through port 314 to a treatment chamber, such as shown in FIGS. 9A and 9B. In an alternative embodiment, chamber 313 itself can be the treatment chamber containing the article(s). In various embodiments, the pathways 118 and 119 can be independently fabricated. The pathways 118 and 119 in various embodiments can also have an optional ground 150 (as previously shown in FIG. 4-7) near the exhaust of the plasma sources to terminate the RF leaking from the sources as the plasma expands. In operation, a gas (e.g., an oxygen-based or halogen-based gas, or an equivalent gas) is supplied to discharge chamber 111 from a suitable source (not shown) and discharge chambers 111 and 311 are optionally supplied with one or more other gases from a suitable source (not shown). RF power from one or more RF energy sources (not shown) is coupled to the discharge chambers 111 and 311 by inductors 115 and 116.

FIG. 9A is a schematic cross-section of a treatment chamber 861 for processing one or more articles, in accordance with one embodiment of the invention. Treatment chamber 861 is coupled to a pathway 118 to receive one or more dissociated gases and distributing them over article(s) 865 on platen 866. A pathway extension 870 has no 90 degree elbow to block photons and directly directs a plasma onto the article 865. In an alternative embodiment of the invention, platen 866 and/or treatment chamber 861 are temperature-controlled to control the temperature of the article(s) 865. Gases are removed from treatment chamber 861 by a suitable vacuum pump (not shown) through one or more exhaust ports 868.

FIG. 9B is a schematic cross-section of a treatment chamber 861 for processing one or more articles, in accordance with an alternative embodiment of the invention. Treatment chamber 861 is coupled to a pathway 118 to receive one or more dissociated gases and distributing them over article(s) 865 on platen 866. A pathway extension 870 has two 90 degree elbows (but in the same plane) to block photons while directing a plasma onto the article 865. In an alternative embodiment of the invention, platen 866 and/or treatment chamber 861 are temperature-controlled to control the temperature of the article(s) 865. Gases are removed from treatment chamber 861 by a suitable vacuum pump (not shown) through one or more exhaust ports 868.

Figure 9C:
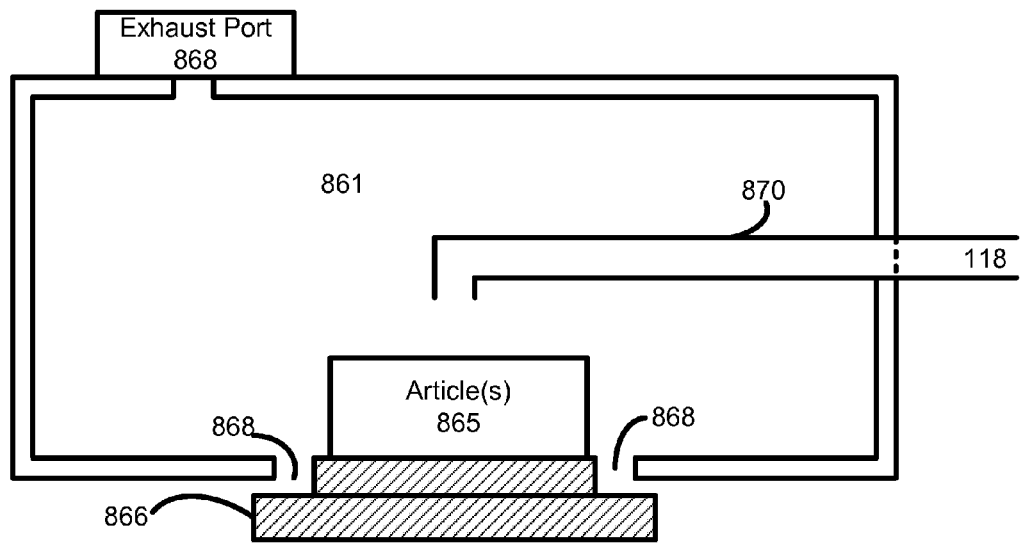
FIG. 9C illustrates a schematic cross-section of a treatment chamber for processing one or more articles, in accordance with another embodiment of the invention.

FIG. 9C is a schematic cross-section of a chamber 861 for processing one or more articles, in accordance with an alternative embodiment of the invention. Treatment chamber 861 is coupled to a pathway 118 to receive one or more dissociated gases and distributing them uniformly over article(s) 865 on platen 866. A pathway extension 870 has at least one 90 degree elbow to block photons and direct a plasma onto the article 865. In an alternative embodiment of the invention, platen 866 and/or treatment chamber 861 are temperature-controlled to control the temperature of the article(s) 865. Gases are removed from treatment chamber 861 by a suitable vacuum pump (not shown) through one or more exhaust ports 868. In an alternative embodiment of the invention, treatment chamber 861 itself contains a plasma (not shown) generated directly in treatment chamber 861, in addition to plasma supplied from other chambers.

Figure 9D:
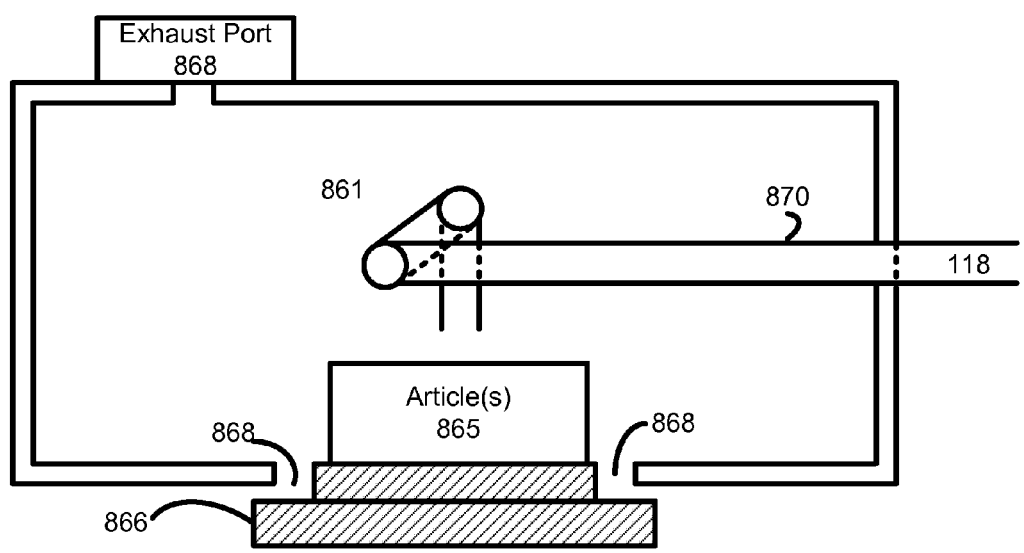
FIG. 9D illustrates a schematic cross-section of a treatment chamber for processing one or more articles, in accordance with another embodiment of the invention.

FIG. 9D is a schematic cross-section of a chamber 861 for processing one or more articles, in accordance with an alternative embodiment of the invention. Treatment chamber 861 is coupled to a pathway 118 to receive one or more dissociated gases and distributing them uniformly over article(s) 865 on platen 866. A pathway extension 870 has a 90 degree elbow in one axis followed by a second 90 degree elbow in a perpendicular axis perpendicular to the plane of the first 90 degree elbow to block photons and direct a plasma onto the article 865. In an alternative embodiment of the invention, platen 866 and/or treatment chamber 861 are temperature-controlled to control the temperature of the article(s) 865. Gases are removed from treatment chamber 861 by a suitable vacuum pump (not shown) through one or more exhaust ports 868. In an alternative embodiment of the invention, treatment chamber 861 itself contains a plasma (not shown) generated directly in treatment chamber 861, in addition to plasma supplied from other chambers.

The invention thus provides apparatus for efficiently concentrating one or more reactive gases in a plasma to provide concentrated plasma to at least one article, without contaminating the sources of the one or more reactive gases. In one embodiment of the invention, an increased density of plasma is created by the concentration of active ions. It will be apparent to those of skill in the art that various modifications can be made in terms of supplying the energy to dissociate the gases and produce plasma. As shown, RF power can be capacitively coupled, rather than inductively coupled, to one or more discharge chambers. Virtually any gas or mixture of gases can be dissociated at sufficient power densities in alternative embodiments of the invention.

Figure 10:
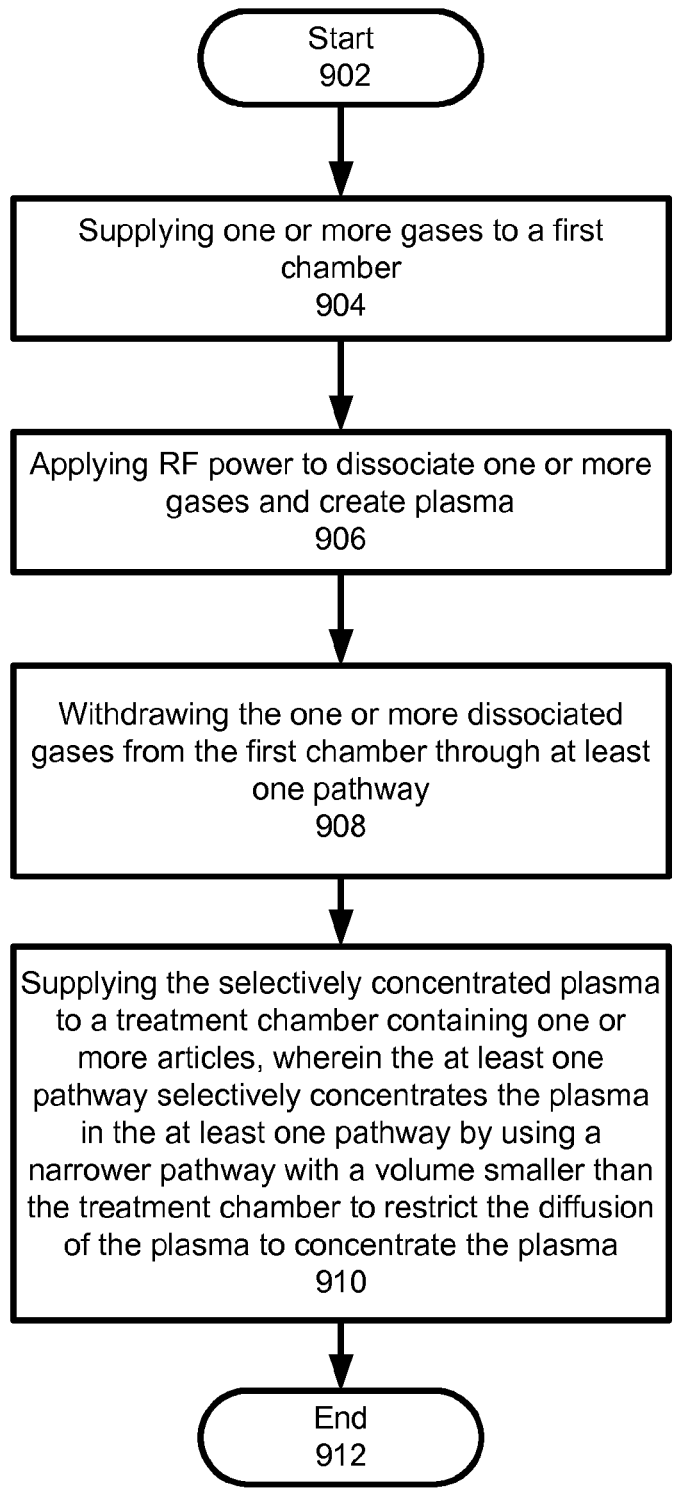
FIG. 10 illustrates a flowchart of a method to generate and concentrate a plasma, according to an alternative embodiment of the invention.

FIG. 10 illustrates a flowchart of a method to provide plasma, according to one embodiment of the invention. The sequence starts in operation 902. Operation 904 includes supplying one or more gases from a source to a first chamber. This operation in some embodiments of the invention would include using a means for controlling (i.e., reducing or preventing) expansion of plasma back through the source from the first chamber. Operation 906 includes applying RF power to dissociate one or more gases and create a plasma. Operation 908 includes withdrawing the one or more dissociated gases from the first chamber through at least one pathway. In one embodiment, the pressure is as low as 1 milliTorr or less. Operation 910 includes supplying the one or more dissociated gases to a treatment chamber containing one or more articles, wherein the at least one pathway selectively concentrates the plasma in the at least one pathway by using a narrower pathway with a volume smaller than the treatment chamber to restrict the diffusion of the plasma to concentrate the plasma. The method ends in operation 912.

Figure 11:
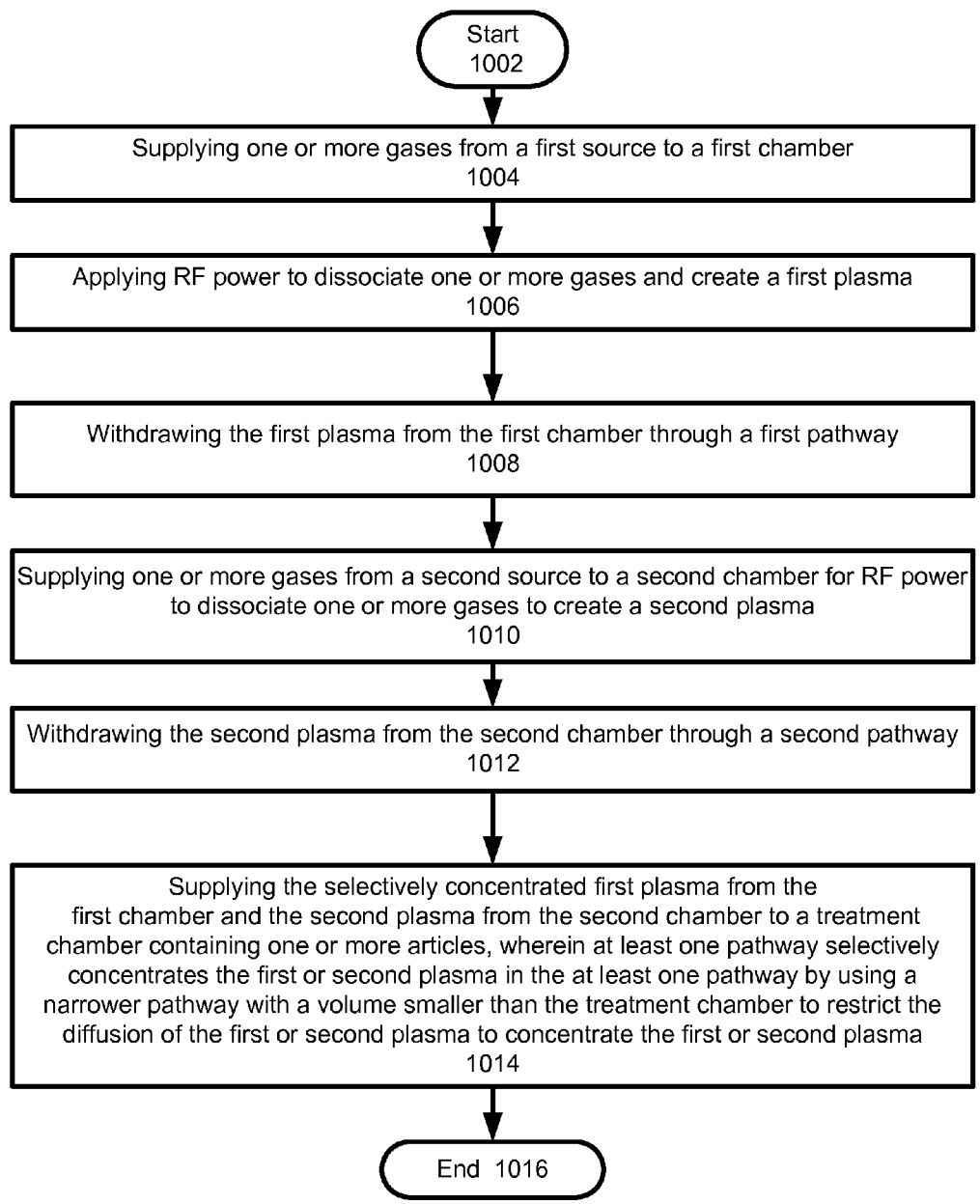
FIG. 11 illustrates a flowchart of a method to generate and concentrate a plasma in parallel, according to an alternative embodiment of the invention.

FIG. 11 illustrates a flowchart of a method to provide plasma, according to an alternative embodiment of the invention. The sequence starts in operation 1002. Operation 1004 is next and includes supplying one or more gases from a first source to a first chamber. Operation 1006 includes applying RF power to dissociate one or more gases and create a first plasma. Operation 1008 includes withdrawing the first plasma from the first chamber through a first pathway. In one embodiment, this could be at a pressure as low as 1 milliTorr or less. Operation 1010 includes supplying one or more gases from a second source to a second chamber for RF power to dissociate one or more gases to create a second plasma. Operation 1012 includes withdrawing the second plasma from the second chamber through a second pathway. In one embodiment, this could be at a pressure as low as 1 milliTorr or less. Operation 1014 includes supplying the first plasma from the first chamber and the second plasma from the second chamber to a treatment chamber containing one or more articles, wherein at least one pathway selectively concentrates the first or second plasma in the at least one pathway by using a narrower pathway with a volume smaller than the treatment chamber to restrict the diffusion of the first or second plasma to concentrate the first or second plasma. The method ends in operation 1016.

In various embodiments of the invention, a pathway can be fabricated with a conducting material with an inner dielectric coating, a dielectric material with an inner metal coating, a conducting material with no inner coating, or a dielectric material with non inner coating. In various embodiments of the invention, a pathway can be fabricated with a straight line of sight between the plasma chamber and the article, or a 90 degree bend in two dimensions between the plasma chamber and the article, or two 90 degree bends in a pathway that has a first 90 degree elbow in one plane, followed by a second 90 degree elbow in the same plane of the first 90 elbow of the pathway between the plasma chamber and the article, or two 90 degree bends in a pathway that has a first 90 degree elbow in one plane, followed by a second 90 degree elbow perpendicular to the plane of the first 90 elbow of the pathway between the plasma chamber and the article. In an alternative embodiment, the first chamber and the second chamber are constructed differently and use either inductive coupling or capacitive coupling to apply RF power to the chambers. In an alternative embodiment, the first chamber and the second chamber are constructed identically.

In one embodiment, a constriction 102 is within an insert 104 that is removable, which can allow the constriction 102 to be disposable, easier to clean, and/or a different material than the material of the pathway. The material used for constructing the constriction 102 can either be reactive or non-reactive with the plasma, as desired. In alternative embodiments of the invention the constriction 102 and insert 104 are a one-piece insert, including a reactive (i.e., reactive to the plasma) or non-reactive material.

In an alternative embodiment, the first chamber and the second chamber are constructed differently and use either inductive coupling or capacitive coupling to apply RF power to the chambers. In an alternative embodiment, the first chamber and second chamber are constructed identically.

The exemplary embodiments described herein are for purposes of illustration and are not intended to be limiting. Therefore, those skilled in the art will recognize that other embodiments could be practiced without departing from the scope and spirit of the claims set forth below.

What is claimed is:

1. A method for treating one or more articles with a selectively concentrated plasma generated from dissociating one or more gases, the method comprising:
   supplying one or more gases from a source to a first chamber;
   applying RF power to dissociate the one or more gases and create a plasma;
   withdrawing the dissociated one or more gases from the first chamber through at least one pathway; and
   supplying the dissociated one or more gases to a treatment chamber containing one or more articles, wherein the at least one pathway selectively concentrates the plasma in the at least one pathway by using a narrower pathway with a volume smaller than the treatment chamber to restrict the diffusion of the plasma to concentrate the plasma, wherein the at least one pathway is comprised of an electrically conducting material or coating to provide a ground path for a plasma to be concentrated.

2. The method of claim 1, further comprising:
   applying RF power to one or more gases in an additional chamber having a second pathway to dissociate the one or more gases from a second source into a second plasma, and withdrawing the second plasma through the second pathway to selectively produce a second concentrated plasma, and to supply the second concentrated plasma to the treatment chamber containing one or more articles, wherein the second pathway selectively concentrates the plasma in the second pathway by using a narrower pathway with a volume smaller than the treatment chamber to restrict the diffusion of the plasma to concentrate the plasma.

3. The method of claim 1, wherein at least one pathway is comprised of a electrically conducting material to provide a ground path for a plasma to be concentrated.

4. The method of claim 3, wherein at least one pathway includes a constriction.

5. The method of claim 1, wherein the pathway has at least one 90 degree elbow.

6. The method of claim 1, wherein the pathway has two 90 degree elbows in the same plane.

7. The method of claim 1, wherein the pathway has a first 90 degree elbow in one plane, followed by a second 90 degree elbow perpendicular to the plane of the first 90 elbow.

8. An apparatus for dissociating one or more gases to produce a plasma, the apparatus comprising:
   a first chamber coupled to a source of one or more gases,
   one or more RF energy sources coupled to the first chamber,
   means for dissociating the one or more gases in the first chamber into a plasma,
   at least one pathway to selectively concentrate the plasma into an concentrated plasma, and
   a treatment chamber coupled to the first chamber through the at least one pathway to receive the concentrated plasma, wherein the treatment chamber can contain one or more articles, wherein the at least one pathway selectively concentrates the plasma in the at least one pathway by using a narrower pathway with a volume smaller than the treatment chamber to restrict the diffusion of the plasma to concentrate the plasma, wherein the at least one pathway is comprised of an electrically conducting material or coating to provide a ground path for a plasma to be concentrated.

9. The apparatus of claim 8, wherein the means for dissociating the one or more gases includes inductively coupling RF energy to the one or more gases in the first chamber.

10. The apparatus of claim 8, wherein the means for dissociating the one or more gases includes a first electrode and a second electrode to capacitively couple RF energy to within the first chamber for dissociating the one or more gases.

11. The apparatus of claim 8, wherein the pathway is comprised of a non-conducting material to concentrate the plasma inside the pathway.

12. The apparatus of claim 8, wherein the pathway is straight with no 90 elbow.

13. The apparatus of claim 8, wherein the pathway has at least one 90 degree elbow.

14. The apparatus of claim 8, wherein the pathway has two 90 degree elbows in the same plane.

15. The apparatus of claim 8, wherein the pathway has a first 90 degree elbow in one plane, followed by a second 90 degree elbow perpendicular to the plane of the first 90 elbow.

16. The apparatus of claim 8, wherein the pressure inside the pathway can be 10 milliTorr or less.

17. An apparatus to dissociate one or more gases to produce plasma, the apparatus comprising:
   a first chamber with a first pathway, wherein the first chamber is coupled to a first source of one or more gases,
   a second chamber with a second pathway, wherein the second chamber is coupled to a second source of one or more gases,
   one or more RF energy sources coupled to the first chamber and the second chamber,
   means for dissociating the one or more gases from the first source of one or more gases into a first plasma in the first chamber,
   means for dissociating the one or more gases from the second source of one or more gases into a second plasma in the second chamber;
   at least one pathway to concentrate at least one plasma from either the first chamber or from the second chamber; and
   a treatment chamber coupled to the first chamber and the second chamber, wherein the treatment chamber contains one or more articles, wherein the at least one pathway selectively concentrates the first or second plasma in the at least one pathway by using a narrower pathway with a volume smaller than the treatment chamber to restrict the diffusion of the first or second plasma to concentrate the first or second plasma, wherein the at least one pathway is comprised of an electrically conducting material or coating to provide a ground path for a plasma to be concentrated.

18. The apparatus of claim 17, wherein at least one pathway has at least one 90 elbow.

19. The apparatus of claim 17, wherein the first chamber and the second chamber supply the first plasma and the second plasma in parallel to the treatment chamber.

20. The apparatus of claim 17, wherein the pressure inside the treatment chamber can be less than 1 milliTorr.

* * * * *